(12) United States Patent
Leonard

(10) Patent No.: US 7,588,603 B2
(45) Date of Patent: Sep. 15, 2009

(54) IMPLANTABLE ORTHESIS AND SURGICAL KIT FOR KNEE ARTHRODESIS

(75) Inventor: Alain Leonard, Caixon (FR)

(73) Assignee: Teknimed, Vic-en-Bigorre (FR)

( * ) Notice: Subject to any disclaimer, the term of this patent is extended or adjusted under 35 U.S.C. 154(b) by 641 days.

(21) Appl. No.: 10/981,603

(22) Filed: Nov. 5, 2004

(65) Prior Publication Data

US 2005/0102031 A1    May 12, 2005

(30) Foreign Application Priority Data

Nov. 5, 2003    (FR) .................................. 03 12997

(51) Int. Cl.
*A61F 2/38*    (2006.01)
*A61F 2/28*    (2006.01)

(52) U.S. Cl. ................ 623/20.21; 623/16.11

(58) Field of Classification Search ............. 623/20.21, 623/20.14, 20.15, 20.16, 20.24, 20.28; 606/62, 606/67, 95
See application file for complete search history.

(56) References Cited

U.S. PATENT DOCUMENTS

| | | | |
|---|---|---|---|
| 3,547,115 A * | 12/1970 | Stevens | ........................ 606/86 |
| 4,676,797 A | 6/1987 | Anapliotis et al. | |
| 4,822,366 A * | 4/1989 | Bolesky | ................... 623/20.15 |
| 5,108,398 A | 4/1992 | McQueen et al. | |
| 6,986,791 B1 * | 1/2006 | Metzger | ................... 623/20.24 |
| 7,141,067 B2 * | 11/2006 | Jones et al. | ............... 623/16.11 |

FOREIGN PATENT DOCUMENTS

| | | | |
|---|---|---|---|
| DE | 197 22 389 | | 12/1998 |
| DE | 199 62 324 | | 7/2001 |
| DE | 19962324 | * | 7/2001 |
| FR | 2 800 987 | | 5/2001 |
| FR | 2800987 | * | 5/2001 |

* cited by examiner

*Primary Examiner*—Corrine M McDermott
*Assistant Examiner*—Megan Wolf
(74) *Attorney, Agent, or Firm*—Young & Thompson

(57) ABSTRACT

The invention relates to an implantable orthesis for knee arthrodesis comprising a tibial anchoring head (1), a femoral anchoring head (2), an intramedullary tibial rod (3) and an intramedullary femoral rod (4). The anchoring heads (1, 2) are of a shape which is without symmetry of revolution and are splayed laterally in a front plane from the intramedullary rod (3, 4). They are rigidly assembled to one another.

23 Claims, 4 Drawing Sheets

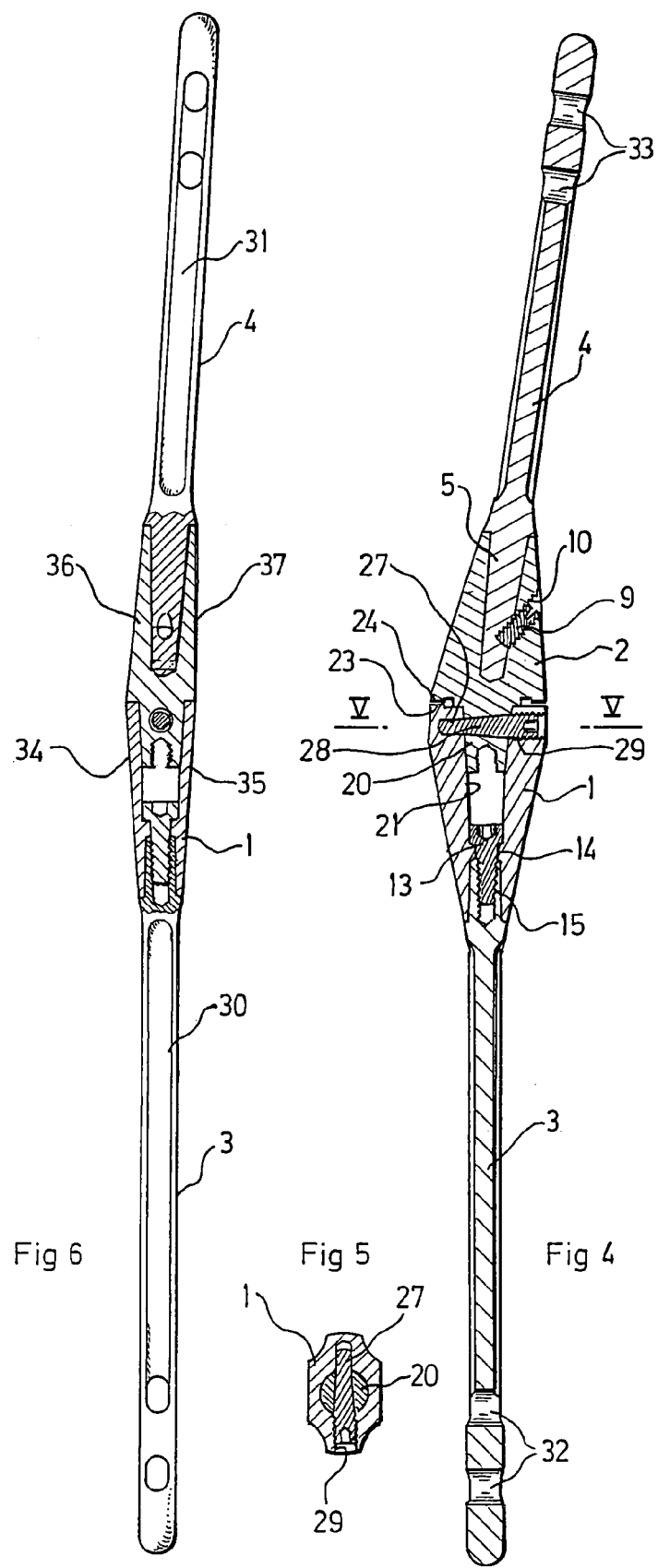

IMPLANTABLE ORTHESIS AND SURGICAL KIT FOR KNEE ARTHRODESIS

FIELD OF THE INVENTION

The invention relates to an implantable orthesis to carry out knee arthrodesis.

BACKGROUND OF THE INVENTION

Knee arthrodesis consists in combining and joining by bone reconstruction the proximal ends of the tibia after resection of the epiphyses.

This operation is advised in the case of severe, in particular infectious, complications following the fitting of articulated prostheses or following major trauma or bone ablations for the treatment of malignant tumours preventing the fitting of prostheses.

The principle of an arthrodesis with the aid of an implantable device consists in implanting a femoro-tibial immobilising material in the metaphyses and medullary parts of the femur and the tibia allowing the immobilised bones to be supported during reconstruction of the peripheral bone and when an intercalary bone graft is carried out.

This implantable immobilising material traditionally consists of an intramedullary nail (Juvara nail) of small diameter, typically 12 mm, allowing maximum bone reconstruction around this nail and of considerable length to be anchored into the medullary canal of the femur and the tibia. However, these nails pose problems with their fitting and with their shapes which are not adapted to natural shapes—in particular to the valgus or flexion angles and the curvature of the femur.

To remedy these problems, FR-2 800 987 has proposed a made-to-measure, two-element implantable device which allows a surgical operation of short duration and causes less post-operative trauma than an intramedullary nail. This device comprises a femoral implant with an intramedullary femoral rod and a tibial implant with an intramedullary tibial rod, in addition to a rigid part connecting the proximal ends of these two implants relative to one another, vertically to the joint. Each intramedullary rod comprises a first distal section of small diameter, a second intermediate section which is slightly in the shape of a truncated cone and a third proximal section of constant section of larger diameter. The rigid connecting part is inserted between the two implants with which it interlocks. It has a cylindrical body with bores manufactured to create the valgus and flexion angles and two anti-rotating radial blades.

This implantable device has the disadvantage of having to be made to size prior to each patient's operation. During the implantation, the quality of the bone of the patient may be worse than expected in view of the examinations and x-rays previously carried out. In fact, arthrodesis is generally a solution considered after multiple operations, the failure of successive prosthetic solutions or following serious trauma to the knee. The implantation site has often been the subject of an infection or multiple infections, having deteriorated the bone tissue, in particular in the region of the proximal ends of the bones. The implantable device prefabricated to size, disclosed by FR-2 800 987, cannot then be fixed. The slightly conical intermediate section of the rods which rests on the medullary canal offers insufficient support and is not axially wedged with sufficient precision in the bone. Despite the fact that the proximal ends of the implants are as unobstructive as possible in the radial direction to facilitate the femoro-tibial peripheral bone reconstruction, this bone reconstruction often proves to be problematical.

In practice, the inventor has established that failures encountered with the aforementioned known implantable device actually stem from insufficient wedging of the implants relative to the bones, from a poor adaptation of the size of the implants in spite of being manufactured to size and from insufficient support of the two bones relative to one another, in particular in torsion.

U.S. Pat. No. 5,108,398 also discloses an implantable device for arthrodesis, of controllable length, comprising a femoral rod, a tibial rod and a screwed-on cylinder for controlling the length of the femoral rod. Here again, the inventor has established that these implants are not sufficiently well wedged relative to the bones and do not create sufficient support, in particular in torsion, in spite of the presence of distal transverse screws.

It is noteworthy moreover that an implantable device for arthrodesis is an orthesis which, in contrast to a prosthetic implant, has the primary purpose of supporting post-operative ankylosis for a sufficient duration to allow the bone reconstruction of the graft between the femur and the tibia (such as external fixings or previously used Juvara nails). In view of this ankylosis it is inconceivable for the implant to withstand all the stresses of walking. Whilst the implantable device of FR-2 800 987 allows the patient to be upright before the end of the reconstruction, it is not designed to withstand all the mechanical stresses connected with walking in the long term. The necessity of this peripheral osteofusion and the specific problems connected to the desired ankylosis mean that the solutions considered for partially or totally articulated prostheses designed to replace all or part of the joint, by ensuring mobility and by withstanding over the long term the mechanical stresses of walking, are badly adapted and cannot be transferred to ortheses for arthodesis. In particular, in an articulated prothesis, the problem of radial obstruction of the implants at the proximal ends does not occur.

DE-19 722 389 has proposed a device for arthrodesis formed in the manner of a secured prosthesis of which the condyles are replaced by fixed plates on intramedullary rods which have symmetry of revolution, these plates axially bearing against the resected proximal ends of the bones, the two plates being attached to one another by a dovetail connection. This device prevents any peripheral bone reconstruction and is singlehandedly supposed to withstand all the long-term femoro-tibial mechanical stresses, which never occur in the case of ankylosis. In fact the two immobilised bones generate between them extremely large mechanical stresses, in particular in flexion and in torsion, and in any case much greater than when a possibility of movement is retained. The device disclosed in this document is destined to break and in any case does not provide anchoring of the implants in the bones which is compatible with maintaining ankylosis, despite the specific implant/bone contact structures recommended by this document. Radial movement is certain to be observed between the implants and the bones in the short or medium term after implantation. The impossibility of using the device of DE-19 722 389 in reality is therefore a practical illustration of how the solutions considered for the protheses cannot be applied in the case of arthrodeses.

SUMMARY OF THE INVENTION

The invention aims to remedy these disadvantages by proposing an implantable orthesis which ensures improved support of the immobilised tibia and the femur, without the risk of subsequent bone damage, whilst allowing and facilitating subsequent osteofusion between the femur and the tibia at the edge of the orthesis between the resected ends of these bones.

The invention also aims to propose such an orthesis which is simple to implant and can be manufactured in a plurality of standard shapes and sizes able to suit the majority of applications without requiring manufacturing to size.

The invention further aims to propose a surgical kit for the fitting of an orthesis according to the invention.

The invention relates therefore to an implantable orthesis for knee arthrodesis comprising a femoral implant containing a femoral rod adapted to be able to be introduced into the medullary canal of the femur, a tibial implant comprising a tibial rod adapted to be able to be introduced into the medullary canal of the tibia, the femoral implant having an adapted proximal fixing end to be able to cooperate with a conjugate proximal fixing end of the tibial implant so as to form a rigid fixing of the two implants relative to one another allowing a peripheral bone reconstruction between the tibia and the femur around these proximal fixing ends, characterised in that:
- the tibial implant has a proximal tibial anchoring head of a shape which is without symmetry of revolution and is splayed in a front plane from the tibial rod, this tibial anchoring head being adapted to be able to be introduced into a splayed cavity of conjugate forms made in the proximal end of the tibia, this tibial anchoring head having a proximal end forming the widest portion of the tibial implant and comprising said proximal fixing end,
- the femoral implant has a proximal femoral anchoring head of a shape which is without symmetry of revolution and is splayed in a front plane from the femoral rod, this femoral anchoring head being adapted to be able to be introduced into a splayed cavity of conjugate forms made in the proximal end of the femur, this femoral anchoring head having a proximal end forming the widest portion of the femoral implant and comprising said proximal fixing end.

The inventor has in fact surprisingly found that the adoption of proximal anchoring heads, splayed in width and without symmetry of revolution, not only does not damage the reconstruction of the peripheral bone but on the contrary, by considerably improving the quality of the relative immobilisation of the tibia to the femur, facilitates this bone reconstruction, for the benefit of a better quality arthrodesis and improved results, even in the most difficult cases. In fact, the splayed anchoring heads fill the internal part of the proximal ends of the bones which have suffered widespread damage following previous prosthetic failures and/or infections and/or trauma and/or disease. Furthermore, they impose a compaction under compression of the damaged bone tissue. Nevertheless, they preserve the generally healthy peripheral epiphysis and metaphysis parts, from which osteofusion is produced on the intercalary bone graft. It is noteworthy in this respect that it is known that if the bone tends to set under the effect of repeated stress under general load, it is however rapidly damaged in the event of localised attack, for example under the effect of movement or concentrated stresses. By avoiding these localised phenomena of movement or concentrated stresses, despite a greater invasive obstruction in the bone, the orthesis according to the invention in fact reinforces the rigidity and the solidity of the arthrodesis obtained.

Advantageously and according to the invention, the tibial anchoring head is formed from a specific part of the tibial rod and the tibial anchoring head and the tibial rod have rigid assembly ends adapted to allow their assembly and their rigid fixing in the extension of one to the other before implantation. Similarly, advantageously and according to the invention, the femoral anchoring head is formed in a specific part of the femoral rod and the femoral anchoring head and the femoral rod have rigid assembly ends adapted to allow their assembly and their rigid fixing in the extension of one to the other before implantation.

In this manner an orthesis according to the invention has great modularity. It is in particular possible to provide a selection of anchoring heads of variable shapes and sizes (for example 2 or 3 tibial rods and between 4 and 8 femoral rods). With such a selection representing a relatively small number of specific parts, a large number (for example between 72 and 2400) of different combinations and thus of ortheses is proposed, enabling the majority of practical cases which can be encountered to be catered for, without the necessity of manufacturing to size.

Advantageously and according to the invention, said rigid assembly ends produce an assembly by relative interlocking (of the head and of the rod) and the orthesis comprises means for relative tightening and securing these ends relative to one another. This interlocking assembly can be cylindrical or truncated cone-shaped.

Similarly, advantageously and according to the invention, the proximal fixing ends of the tibial anchoring head and the femoral anchoring head are adapted to be able to be assembled and rigidly fixed relative to one another by relative interlocking after implantation of the tibial implant and the femoral implant. Advantageously and according to the invention, the orthesis comprises means for relative tightening and securing of the proximal ends of fixation relative to one another, in particular in the form of a lateral screw adapted to extend into the bores made in the tibial and femoral anchoring heads and oriented in a front plane, one of these bores being threaded. Here again, the assembly can be cylindrical or truncated cone-shaped. The screw is advantageously splayed so as to produce relative axial tightening of the anchoring heads as it is tightened.

Advantageously and according to the invention, at least one of the anchoring heads—particularly the two anchoring heads—is(are) of splayed shape in a sagittal plane from the corresponding tibial or femoral rod, with a sagittal splay angle less than the front splay angle such that the proximal fixing end has a lower sagittal depth than its front width.

Advantageously and according to the invention, at least one of the anchoring heads—particularly the two anchoring heads—comprise(s) two front and rear front flats extending with a sagittal splay angle relative to one another.

Advantageously and according to the invention, at least one of the anchoring heads—particularly the two anchoring heads—comprise(s) at least one longitudinal groove.

Advantageously and according to the invention, at least one of the anchoring heads—particularly the two anchoring heads—comprise(s) four angled longitudinal grooves with an arcuate transverse cross-section along the longitudinal edges of each flat.

The invention extends to a surgical kit for a knee arthrodesis, characterised in that it comprises a plurality of prefabricated implantable ortheses according to the invention of different sizes and/or shapes. Advantageously and according to the invention, this kit comprises a plurality of tibial anchoring heads, a plurality of femoral anchoring heads, a plurality of tibial rods and a plurality of femoral rods, of different sizes and/or shapes.

Moreover, advantageously and according to the invention, the kit comprises templates representing each orthesis part which it contains, adapted to allow the choice of prefabricated implantable orthesis by superimposing with an x-ray. Equally, a kit according to the invention comprises a plurality of adapted ancillary parts, each for the fitting of one of the parts of the prefabricated implantable orthesis.

The invention extends to an implantable orthesis for arthrodesis and to a surgical kit characterised in combination by all or part of the features mentioned above or below.

BRIEF DESCRIPTION OF THE DRAWINGS

Other aims, advantages and features of the invention will emerge by reading the following description which refers to the accompanying drawings, in which:

FIG. 4 is a front sectional diagrammatic view of an orthesis according to the invention, FIG. 5 is a diagrammatic view along the line V-V of FIG. 4, FIG. 6 is a sagittal diagrammatic view in section of an orthesis according to the invention.

DETAILED DESCRIPTION OF THE PREFERRED EMBODIMENTS

Figure 1:
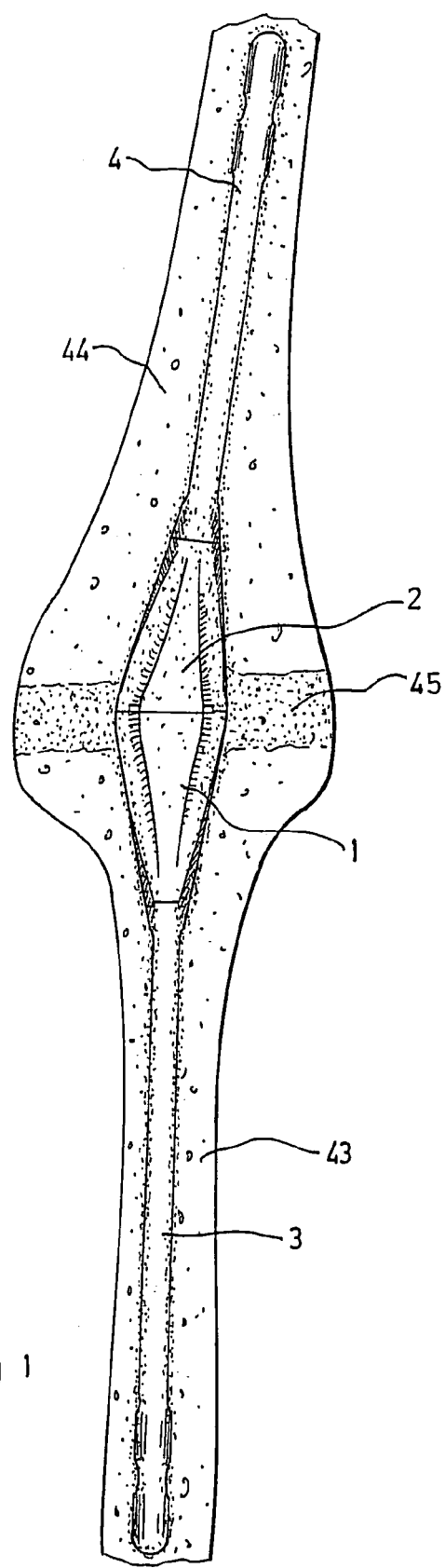
FIG. 1 is a front diagrammatic view of an orthesis according to the invention after implantation.

The orthesis according to the invention shown in the Figures comprises a proximal tibial anchoring head 1, a proximal femoral anchoring head 2, a distal tibial intramedullary rod 3 and a distal femoral intramedullary rod 4. It is thus composed of four principal parts, in addition to three screws 9, 13, 28 for securing and tightening these parts to one another.

To avoid any errors of assembly, the fasteners of the tibial rod 3 onto the tibial anchoring head 1 are not compatible with the fasteners of the femoral rod on the femoral anchoring head 2.

For the assembly of the femoral anchoring head 2 on the intramedullary femoral rod 4, the latter is equipped with a male assembly cone 5 adapted so as to be able to be introduced into a conjugate female cone 6 of the femoral anchoring head 2. The end of the male cone 5 has a depression 7 forming a bearing support 8 for the free end of a tightening screw 9 introduced into a threaded bore 10 of the femoral anchoring head 2. The axis of this threaded bore 10 is inclined relative to the axis of the cones 5, 6 such that when the screw 9 is tightened, its free end bears against the bearing support 8 by axially tightening the two cones 5, 6 into one another.

The intramedullary tibial rod 3 comprises a male cylinder 11 at its proximal end adapted to be able to penetrate into a female cylinder 12 made in the tibial anchoring head 1, for the assembly of the tibial rod 3 on this tibial anchoring head 1. An axial tightening screw 13 can be axially introduced through the tibial head 1 so as to bear on a shoulder 14 thereof and so that its threaded end can be introduced into a threaded bore 15 of the cylinder 11 for assembling the tibial rod 3. When the screw 13 is tightened, the tibial rod 3 is assembled tightened on the tibial anchoring head 1. Moreover, the tibial head 1 and the tibial rod 3 have notches 16, respectively 17, and conjugate projections 18, respectively 19, securing the tibial head 1 relative to the tibial rod 3 in axial rotation.

The femoral anchoring head 2 comprises a male cone trunk 20 adapted to be able to be introduced into a conjugate female cone trunk 21 of the tibial anchoring head 1, with a view to a smooth conical-type assembly between these two heads 1, 2.

The proximal fixing end 22 of the tibial anchoring head 1 advantageously has an axial lateral projection 23 designed to be housed in a conjugate reinforcement 24 of the proximal fixing end 25 of the femoral head 2. This projection 23 and this reinforcement 24 therefore constitute an alignment device preventing any reverse assembly.

The cone trunk 20 of the femoral anchoring head 2 comprises a splayed radial transverse bore 26, in particular substantially truncated cone-shaped, adapted to receive the free end. This screw 28 is pointed, in particular a substantially truncated cone-shaped 27 screw 28 for securing and tightening the two assembled heads 1, 2. This screw 28 is tightened in a radial transverse threaded bore 29 of the tibial anchoring head 1. Being pointed, in other words splayed opposite its free end 27, when it is screwed it causes the axial tightening of the two anchoring heads 1, 2, as it is screwed into the bore 26.

The threaded bore 29 is positioned so as to be opposite the bore 26 of the cone trunk 20 of the femoral anchoring head 2 when the latter is assembled on the tibial anchoring head 1. The threaded bore 29 opens out laterally to the exterior, in other words on the side of the tibial anchoring head 1, such that it is accessible from the side of the orthesis during the implantation. It is arranged in the vicinity of the proximal fixing end 22 of the tibial anchoring head 1 which generally protrudes, after implantation of the tibial implant, beyond the tibia 43, in other words beyond the resected part of the proximal end of the tibia 43. In this manner the screw 28 is accessible for tightening after implantation of the tibial implant 1, 3.

The femoral anchoring head 2 is adapted to create a valgus angle and a flexion angle, in other words the respective axes of its cone trunk 20 for assembling on the tibial anchoring head 1 and of its female cone trunk 6 for assembling to the femoral rod 4 are oriented so as to create these angles.

The femoral rod 4 can also have a curvature conforming to the natural curvature of the femur 44. Each of the rods 3, 4 is equipped with lateral longitudinal grooves 30, respectively 31, in addition to transverse distal through-bores 32, respectively 33, allowing them to be distally fixed by transverse screws in a manner known per se.

The tibial 1 and femoral anchoring heads 2 have a front splay angle at the top (angle at the top of the trapezium which defines the front axial section of the head 1, 2) which is between 20 degrees and 45 degrees, and more particularly, in the preferred embodiments, between 22 degrees and 37 degrees.

Each anchoring head 1, 2 is in fact splayed from its end for assembling to the corresponding rod 3, 4, as far as its respective proximal fixing end 22, 25, which forms the widest portion of this head 1, 2 and thus of the orthesis. The anchoring heads 1, 2 have at their proximal fixing end 22, 25 a front width between 20 mm and 40 mm—in particular in the order of 30 mm.

The anchoring heads 1, 2 are also of splayed shape in the sagittal plane, from the corresponding intramedullary rod 1, 4 with a sagittal splay angle less than the front splay angle, such that the proximal fixing end 22, 25 has a sagittal depth less than its front width. The sagittal splay angle at the top (angle at the top of the trapezium which defines the sagittal axial section of the head 1, 2) is advantageously between 10 degrees and 25 degrees and more particularly in the preferred embodiments, between 13 degrees and 23 degrees. The anchoring heads 1, 2 have at their proximal fixing end 22, 25 a sagittal depth which can be between 15 mm and 25 mm, in particular in the order of 18 mm.

The anchoring heads 1, 2 each comprise two anterior 34, 36 and rear front flats 35, 37 respectively, extending with a sagittal splay angle relative to one another. In a variant not shown, these flats can be more or less skew, concave or convex in axial or transverse section.

Moreover, each of these anchoring heads 1 comprises four angled longitudinal grooves 38, respectively 39, with an arcuate concave transverse section, in particular circular, along the longitudinal edges of each flat 34, 35, 36, 37. These longitudinal angled grooves 38, 39 facilitate the insertion of anchoring heads 1, 2 in the bone 43, 44, 45 by reinforcing their torsional securing.

Preferably, as shown, each anchoring head 1, 2 has a section in an axial front plane which is trapezoidal or substantially trapezoidal. Each anchoring head 1, 2 can be thus formed from one truncated cone-shaped part or substantially truncated cone-shaped on which the flats 34, 36, 35, 37 and the angled grooves 38, 39 have been formed. Nevertheless other splayed shapes, for example concave or convex, are possible.

The right transverse section of the tibial and femoral rods 3, 4 which is without symmetry in revolution, in addition to the possible distal transverse screws, reinforce the torsional securing of these rods 3, 4 relative to the bones 43, 44. Each tibial and femoral rod 3, 4 preferably has a right transverse section of at least substantially constant size along this rod 3, 4, with the possible exception of a fillet 40, 41 on the corresponding anchoring head 1, 2. This fillet 40, 41 does not exist if the diameter of the intramedullary rod is the same as that of the distal end of the corresponding anchoring head 1, 2.

The following table 1 gives an example of different possible sizings in millimetres of different parts forming an orthesis according to the invention.

|  |  | Associated Leg | Diameter | Length | Curvature |
|---|---|---|---|---|---|
| Tibial Implant | Rod | Any | 9.5 | 165 |  |
|  |  | Any | 11.5 | 165 |  |
|  | Head | Any |  | 45 |  |
|  |  | Any |  | 50 |  |
|  |  | Any |  | 55 |  |
|  |  | Any |  | 60 |  |
|  |  | Any |  | 65 |  |
| Femoral Implant | Rod | Any | 10 | 130 | 900 |
|  |  | Any | 12 | 130 | 900 |
|  |  | Any | 14 | 130 | 900 |
|  |  | Any | 10 | 160 | 900 |
|  |  | Any | 10 | 160 | 1050 |
|  |  | Any | 12 | 160 | 900 |
|  |  | Any | 12 | 160 | 1050 |
|  |  | Any | 14 | 160 | 900 |
|  |  | Any | 14 | 160 | 1050 |
|  | Head | Left |  | 45 |  |
|  |  | Left |  | 60 |  |
|  |  | Right |  | 45 |  |
|  |  | Right |  | 60 |  |

All the parts corresponding to this range can be assembled in a container forming a surgical kit, the surgeon selecting the parts of appropriate size, even during the operation, according to requirements. The length of the parts to obtain stabilisation of the limb is determined by taking into account a shortening of 2 cm. The diameters of the rods 3, 4 and the dimensions of the heads 1, 2 are adapted according to the bone morphology and the quality of the bone tissue.

As a variant, it is also possible to provide several lateral and sagittal dimensions for the anchoring heads.

Figure 2:
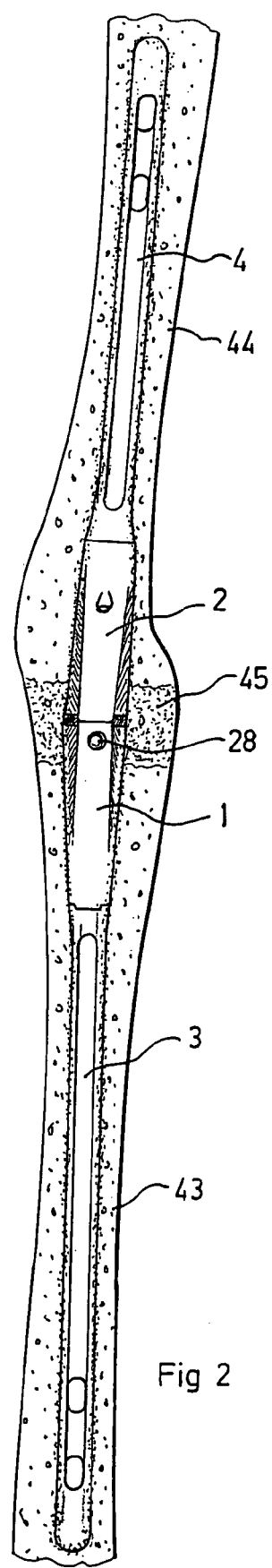
FIG. 2 is a sagittal diagrammatic view of an orthesis.
Figure 3:
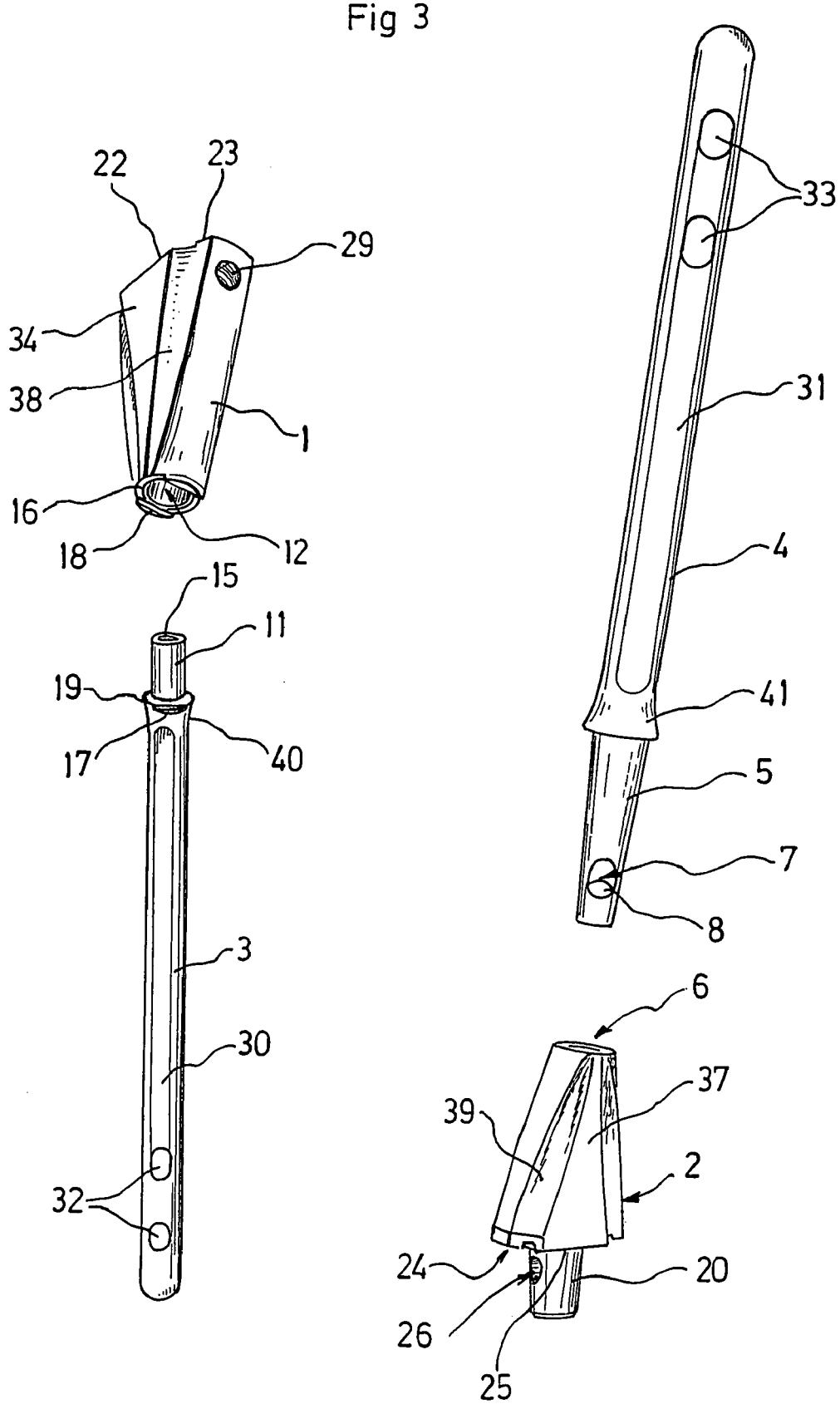
FIG. 3 is an exploded perspective diagrammatic view of an orthesis according to the invention.

As is seen in FIGS. 1 and 2, the length of the tibial 1, 3 and femoral 2, 4 implants rigidly assembled to one another by the fixing ends 22, 25 of the anchoring heads 1, 2 determines the total femoral width of the leg. Between the proximal resected end of the tibia 43 and that of the femur 44, a bone graft 45 and/or any osteoconductive material can be inserted around the parts of the anchoring heads 1, 2 protruding beyond the tibia 43 and the femur 44. The orthesis supports the bones, 43, 44 immobilised during the taking of the graft 45 which then ensures the support and the ankylosis.

The surgical kit according to the invention also advantageously comprises templates which each represent these parts in front section and sagittal section, which can be superimposed by x-rays of the patient to facilitate the choice of parts even before the surgical operation. Also, the surgical kit according to the invention comprises ancillary material allowing the preparation of the bones and the fitting of the orthesis. This ancillary material can in particular comprise raspatories of similar shape to those of the heads 1, 2 designed only to be maneuvered axially to the interior of the bones to create cavities for receiving the anchoring heads 1, 2. It can also comprise guides for drilling in the medullary canals and directional vices.

The surface of the anchoring heads 1, 2 in contact with the bones in addition to that of the rods 3, 4 can be left smooth or on the other hand coated with a coating facilitating osteo integration, in particular a hydroxyapatite coating or the like.

The conical assembly of the two anchoring heads 1, 2 onto one another is adapted to allow the interlocking of the cone trunks 20, 21 with one another by moving from the position of the tibia bent at 90 degrees relative to the femur, a position in which the implantation of the tibial implant 1, 3 and the femoral implant 2, 4 is carried out.

The tibial anchoring head 1 is assembled and tightened on the tibial rod 3 before its implantation in the tibia. Similarly, the femoral anchoring head 2 is assembled by tightening on the femoral rod 4 before the implantation in the femur. After assembly and tightening of the two heads 1, 2 by the screw 28, the two bones are held immobilised relative to one another with the appropriate valgus and flexion angles defined by the femoral anchoring head 2.

Despite the relatively large obstruction of the anchoring heads 1, 2 at the proximal ends of the bones, in practice excellent bone reconstruction is seen and high quality fusion between the tibia and the femur, resulting within a short space of time in an arthrodesis which is also of high quality.

The patient can be upright soon (typically 24 hours) after the surgical operation, due to the excellent fixing created by the orthesis according to the invention.

The invention can be the subject of numerous variants relative to the preferred embodiments disclosed above and shown in the figures.

The invention claimed is:

1. An implantable orthesis for knee arthrodesis comprising a femoral implant containing a femoral rod adapted to be able to be introduced into the medullary canal of the femur, a tibial implant comprising a tibial rod adapted to be able to be introduced into the medullary canal of the tibia, the femoral implant having a proximal fixing end adapted to be able to cooperate with a conjugate proximal fixing end of the tibial implant so as to form a rigid fixing of the two implants relative to one another allowing peripheral bone reconstruction between the tibia and the femur and around these proximal fixing ends, wherein:

the tibial implant has a proximal tibial anchoring head of a shape which is without symmetry of revolution and splayed in a front plane from the tibial rod, this tibial anchoring head being adapted to be able to be introduced into a splayed cavity of forms made in the proximal end of the tibia, this tibial anchoring head having a proximal end forming the widest portion of the tibial implant and constituting said proximal fixing end;

the femoral implant has a proximal femoral anchoring head of a shape which is without symmetry of revolution and splayed in a front plane from the femoral rod, this femoral anchoring head being adapted to be able to be introduced into a splayed cavity of conjugate forms made in the proximal end of the femur, this femoral anchoring head having a proximal end forming the widest portion of the femoral implant and constituting said proximal fixing end;

the tibial and femoral anchoring heads have a front splay angle at a top of a trapezium which defines a front axial section of the tibial and femoral anchoring heads of between 20 degrees and 45 degrees, and at least one of the anchoring heads is of splayed shape in a sagittal plane from the corresponding tibial or femoral rod, with a sagittal splay angle less than the front splay angle such that the proximal fixing end has a lower sagittal depth than a front width.

2. The orthesis as claimed in claim 1, wherein the tibial anchoring head is formed from a specific part of the tibial rod, the tibial anchoring head and tibial rod having rigid assembly ends adapted to allow their assembly and their rigid fixing in the extension of one to the other before implantation.

3. The orthesis as claimed in claim 2, wherein the rigid assembly ends produce an assembly by relative interlocking and further comprising means for the relative tightening and securing of these ends relative to one another.

4. The orthesis as claimed in claim 1, wherein the femoral anchoring head is formed from a specific part of the femoral rod, the femoral anchoring head and the femoral rod having rigid assembly ends adapted to allow their assembly and their rigid fixing in the extension of one to the other before implantation.

5. The orthesis as claimed in claim 4, wherein the rigid assembly ends produce an assembly by relative interlocking and in that it comprises means for relative tightening and securing of these ends relative to one another.

6. The orthesis as claimed in claim 1, wherein the sagittal splay angle at the top is between 10 degrees and 25 degrees.

7. The orthesis as claimed in claim 1, wherein the anchoring heads have at their proximal fixing end a front width between 20 mm and 40 mm.

8. The orthesis as claimed in claim 1, wherein the anchoring heads have at their proximal fixing end a sagittal depth of between 15 mm and 25 mm.

9. The orthesis as claimed in claim 1, wherein at least one of the tibial and femoral anchoring heads comprises front and rear front flats extending with a sagittal splay angle relative to one another.

10. The orthesis as claimed in claim 9, wherein at least one of the anchoring heads comprises four angled longitudinal grooves with an arcuate transverse cross-section along the longitudinal edges of each flat.

11. The orthesis as claimed in claim 1, wherein at least one of the anchoring heads comprises at least one longitudinal groove.

12. The orthesis as claimed in claim 1, wherein the proximal fixing ends of the tibial anchoring head and the femoral anchoring head are adapted to be able to be assembled and fixed rigidly to one another by relative interlocking after implantation of the tibial implant and the femoral implant.

13. The orthesis as claimed in claim 12, further comprising means for relative securing and tightening of the proximal fixing ends relative to one another.

14. The orthesis as claimed in claim 12, further comprising a lateral screw for relative securing and tightening of the proximal fixing ends relative to one another, said lateral screw being adapted to extend into bores made in the tibial and femoral anchoring heads oriented in a front plane, one of these bores being threaded.

15. The orthesis as claimed in claim 14, wherein the lateral screw has a splayed end so as to produce relative axial tightening of the anchoring heads as said lateral screw is screwed in.

16. The orthesis as claimed in claim 1, wherein one of the anchoring heads comprises a male cone trunk of adapted assembly to be able to be introduced into a female cone trunk of conjugate assembly of the other anchoring head, such that their relative assembly is of conical type.

17. The orthesis as claimed in claim 1, wherein the tibial and femoral rods have a right transverse section which is without symmetry in revolution.

18. The orthesis as claimed in claim 1, wherein the tibial and femoral rods have a right transverse section of at least substantially constant size along the rod.

19. A surgical kit for knee arthrodesis, comprising a plurality of prefabricated implantable ortheses according to claim 1, of different sizes and/or shapes.

20. The surgical kit as claimed in claim 19, further comprising a plurality of tibial anchoring heads, a plurality of femoral anchoring heads, a plurality of tibial rods, a plurality of femoral rods of different sizes and/or shapes.

21. The surgical kit as claimed in claim 19, further comprising templates representing each part of the orthesis that the surgical kit contains, adapted to allow the selection of the prefabricated implantable orthesis by superimposing with an x-ray.

22. The surgical kit as claimed in claim 19, further comprising a plurality of ancillary parts each adapted to the fitting of one of the prefabricated implantable ortheses.

23. An implantable orthesis for knee arthrodesis comprising a femoral implant containing a femoral rod adapted to be able to be introduced into the medullary canal of the femur, a tibial implant comprising a tibial rod adapted to be able to be introduced into the medullary canal of the tibia, the femoral implant having a proximal fixing end adapted to be able to cooperate with a conjugate proximal fixing end of the tibial implant so as to form a rigid fixing of the two implants relative to one another allowing peripheral bone reconstruction between the tibia and the femur and around these proximal fixing ends, wherein:

the tibial implant has a proximal tibial anchoring head of a shape which is without symmetry of revolution and splayed in a front plane from the tibial rod, this tibial anchoring head being adapted to be able to be introduced into a splayed cavity of forms made in the proximal end of the tibia, this tibial anchoring head having a proximal end forming the widest portion of the tibial implant and constituting said proximal fixing end;

the femoral implant has a proximal femoral anchoring head of a shape which is without symmetry of revolution and splayed in a front plane from the femoral rod, this femoral anchoring head being adapted to be able to be introduced into a splayed cavity of conjugate forms made in the proximal end of the femur, this femoral anchoring head having a proximal end forming the widest portion of the femoral implant and constituting said proximal fixing end; and the tibial and femoral anchoring heads each have a splayed shape in a sagittal plane from the corresponding tibial or femoral rod, with a sagittal splay angle less than the front splay angle such that the proximal fixing end has a lower sagittal depth than a front width.

\* \* \* \* \*

UNITED STATES PATENT AND TRADEMARK OFFICE
CERTIFICATE OF CORRECTION

PATENT NO. : 7,588,603 B2 Page 1 of 1
APPLICATION NO. : 10/981603
DATED : September 15, 2009
INVENTOR(S) : Alain Leonard It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1233 days.

Signed and Sealed this

Twenty-first Day of September, 2010

David J. Kappos
*Director of the United States Patent and Trademark Office*